(12) United States Patent
Corl (10) Patent No.: US 8,864,674 B2
(45) Date of Patent: Oct. 21, 2014

(54) CIRCUIT ARCHITECTURES AND ELECTRICAL INTERFACES FOR ROTATIONAL INTRAVASCULAR ULTRASOUND (IVUS) DEVICES

(71) Applicant: Volcano Corporation, San Diego, CA (US)

(72) Inventor: Paul Douglas Corl, Palo Alto, CA (US)

(73) Assignee: Volcano Corporation, San Diego, CA (US)

( * ) Notice: Subject to any disclaimer, the term of this patent is extended or adjusted under 35 U.S.C. 154(b) by 0 days.

(21) Appl. No.: 13/892,045

(22) Filed: May 10, 2013

(65) Prior Publication Data
US 2013/0303919 A1 Nov. 14, 2013

Related U.S. Application Data

(60) Provisional application No. 61/646,062, filed on May 11, 2012.

(51) Int. Cl.
| | |
|---|---|
| *A61B 8/14* | (2006.01) |
| *A61B 8/00* | (2006.01) |
| *A61B 8/12* | (2006.01) |
| A61B 8/08 | (2006.01) |

(52) U.S. Cl.
CPC .............. *A61B 8/4494* (2013.01); *A61B 8/4461* (2013.01); *A61B 8/52* (2013.01); *A61B 8/12* (2013.01); *A61B 8/445* (2013.01)
USPC .......................................................... 600/462

(58) Field of Classification Search
CPC ...... A61B 8/4461; A61B 8/4483; A61B 8/00; A61B 8/4494; A61B 8/54; A61B 8/56; A61B 8/52; A61B 8/445; A61B 8/12
USPC .......... 600/407, 411, 423, 427, 433–435, 437, 600/459, 466; 606/14, 15, 16
See application file for complete search history.

(56) References Cited

U.S. PATENT DOCUMENTS

| | | | |
|---|---|---|---|
| 4,818,820 A * | 4/1989 | LaRock | .......................... 174/36 |
| 5,924,993 A | 7/1999 | Hadjicostis et al. | |
| 2001/0016688 A1 | 8/2001 | Moore et al. | |
| 2002/0087083 A1 | 7/2002 | Nix et al. | |
| 2008/0025145 A1 | 1/2008 | Peszynski et al. | |
| 2010/0168583 A1 | 7/2010 | Dausch et al. | |
| 2010/0234736 A1 | 9/2010 | Corl | |

OTHER PUBLICATIONS

International Searching Authority/KIPO, "Notification of Transmittal of the International Search Report and the Written Opinion of the International Searching Authority, or the Declaration," for PCT/US2013/040554, mailed Aug. 27, 2013, 13 pages.

* cited by examiner

*Primary Examiner* — Elmer Chao
(74) *Attorney, Agent, or Firm* — Haynes and Boone, LLP (57) ABSTRACT

Rotational intravascular ultrasound (IVUS) imaging devices, systems, and methods are provided. Some embodiments of the present disclosure are particularly directed to compact and efficient circuit architectures and electrical interfaces for polymer piezoelectric micromachined ultrasonic transducers (PMUTs) used in rotational IVUS systems. In one embodiment, a rotational intravascular ultrasound (IVUS) device includes: a flexible elongate member; a piezoelectric micromachined ultrasound transducer (PMUT) coupled to a distal portion of the flexible elongate member; and an application-specific integrated circuit (ASIC) coupled to the distal portion of the flexible elongate member. The ASIC is electrically coupled to the PMUT and includes a pulser, an amplifier, a protection circuit, and timing and control circuitry for coordinating operation of the pulser, amplifier, and protection circuit.

25 Claims, 7 Drawing Sheets

CIRCUIT ARCHITECTURES AND ELECTRICAL INTERFACES FOR ROTATIONAL INTRAVASCULAR ULTRASOUND (IVUS) DEVICES

CROSS-REFERENCE TO RELATED APPLICATIONS

The present application claims priority to and the benefit of U.S. Provisional Patent Application No. 61/646,062, filed May 11, 2012, which is hereby incorporated by reference in its entirety.

TECHNICAL FIELD

The present disclosure relates generally to intravascular ultrasound (IVUS) imaging inside the living body and, in particular, to an intravascular ultrasound imaging catheter that relies on a mechanically-scanned ultrasound transducer, including embodiments where the transducer is a piezoelectric micromachined ultrasound transducer (PMUT) based on a polymer piezoelectric. A PMUT using polymer piezoelectric material suitable for IVUS imaging is not capable of efficiently driving the long electrical cable from the distal end of the catheter back to the patient interface module at the proximal end of the catheter. Therefore, the PMUT requires active electronics (an amplifier circuit) closely coupled to the transducer. The present disclosure provides circuit architectures and electrical interfaces that are particularly well-suited for connecting a polymer-based PMUT to a rotational IVUS imaging system.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. IVUS imaging uses ultrasound echoes to form a cross-sectional image of the vessel of interest. Typically, the ultrasound transducer on an IVUS catheter both emits ultrasound pulses and receives the reflected ultrasound echoes. The ultrasound waves pass easily through most tissues and blood, but they are partially reflected by discontinuities arising from tissue structures (such as the various layers of the vessel wall), red blood cells, and other features of interest. The IVUS imaging system, which is connected to the IVUS catheter by way of a patient interface module, processes the received ultrasound echoes to produce a cross-sectional image of the vessel where the catheter is located.

There are two types of IVUS catheters in common use today: solid-state and rotational, with each having advantages and disadvantages. Solid-state IVUS catheters use an array of ultrasound transducers (typically 64) distributed around the circumference of the catheter and connected to an electronic multiplexer circuit. The multiplexer circuit selects array elements for transmitting an ultrasound pulse and receiving the echo signal. By stepping through a sequence of transmit-receive pairs, the solid-state IVUS system can synthesize the effect of a mechanically scanned transducer element, but without moving parts. Since there is no rotating mechanical element, the transducer array can be placed in direct contact with the blood and vessel tissue with minimal risk of vessel trauma and the solid-state scanner can be wired directly to the imaging system with a simple electrical cable and a standard detachable electrical connector.

In the typical rotational IVUS catheter, a single ultrasound transducer element fabricated from a piezoelectric ceramic material is located at the tip of a flexible driveshaft that spins inside a plastic sheath inserted into the vessel of interest. The transducer element is oriented such that the ultrasound beam propagates generally perpendicular to the axis of the catheter. The fluid-filled sheath protects the vessel tissue from the spinning transducer and driveshaft while permitting ultrasound signals to freely propagate from the transducer into the tissue and back. As the driveshaft rotates (typically at 30 revolutions per second), the transducer is periodically excited with a high voltage pulse to emit a short burst of ultrasound. The same transducer then listens for the returning echoes reflected from various tissue structures, and the IVUS imaging system assembles a two dimensional display of the vessel cross-section from a sequence of several hundred of these ultrasound pulse/echo acquisition sequences occurring during a single revolution of the transducer.

While the solid-state IVUS catheter is simple to use, thanks to its lack of moving parts, it cannot match the image quality available from a rotational IVUS catheter. It is difficult to operate a solid-state IVUS catheter at the same high frequency as a rotational IVUS device, and the lower operating frequency of solid-state IVUS catheters translates into poorer resolution compared to that of a higher frequency rotational IVUS catheter. There are also artifacts such as sidelobes, grating lobes, and poor elevation focus (perpendicular to the imaging plane) that arise from the array-based imaging that are greatly reduced or completely absent with a rotational IVUS device. Despite the image quality advantages of the rotational IVUS catheter, each of these devices has found a niche in the interventional cardiology market, with solid-state IVUS preferred in circumstances where ease-of-use is paramount and the reduced image quality is acceptable for the particular diagnostic needs, while rotational IVUS is preferred where image quality is paramount and the more time-consuming catheter preparation is justified.

In the rotational IVUS catheter, the ultrasound transducer is typically a piezoelectric ceramic element with low electrical impedance capable of directly driving an electrical cable connecting the transducer to the imaging system hardware. In this case, a single pair of electrical leads (or coaxial cable) is used to carry the transmit pulse from the system to the transducer and to carry the received echo signals from the transducer back to the imaging system by way of a patient interface module, where they are assembled into an image. An important complication in this electrical interface is the transportation of electrical signals across a rotating mechanical junction. Since the catheter driveshaft and transducer are spinning (in order to scan a cross-section of the artery) and the imaging system hardware is stationary, there must be an electromechanical interface where the electrical signals traverse the rotating junction. In rotational IVUS imaging systems, this problem can be solved by a variety of different approaches, including the use of a rotary transformer, slip rings, rotary capacitors, etc.

While existing IVUS catheters deliver useful diagnostic information, there is a need for enhanced image quality to provide more valuable insight into the vessel condition. For further improvement in image quality in rotational IVUS imaging, it is desirable to use a transducer with broader bandwidth and to incorporate focusing into the transducer. The piezoelectric micromachined ultrasound transducer (PMUT) fabricated using a polymer piezoelectric material, such as disclosed in U.S. Pat. No. 6,641,540, offers greater than 100% bandwidth for optimum resolution in the radial direction, and a spherically-focused aperture for optimum azimuthal and elevation resolution. While this polymer PMUT technology offers many advantages, the electrical impedance of the transducer is too high to efficiently drive the electrical cable connecting the transducer to the IVUS imaging system by way of the PIM. Furthermore, the transmit efficiency of polymer piezoelectric material is much lower compared to that of the traditional lead-zirconate-titanate (PZT) ceramic piezoelectric, therefore the signal-to-noise ratio will be compromised unless the deficiency in acoustic output can be compensated by improved transmit electronics or other signal processing advances.

Accordingly, there remains a need for improved devices, systems, and methods for providing a compact and efficient circuit architecture and electrical interface to a polymer piezoelectric micro-machined ultrasonic transducer used in an intravascular ultrasound system.

SUMMARY

Embodiments of the present disclosure provide a compact and efficient circuit architecture and electrical interface to a polymer piezoelectric micro-machined ultrasonic transducer used in an intravascular ultrasound system.

In one embodiment, a rotational intravascular ultrasound (IVUS) device is provided. The rotational IVUS device comprises: a flexible elongate member; a piezoelectric micromachined ultrasound transducer (PMUT) coupled to a distal portion of the flexible elongate member; and an application-specific integrated circuit (ASIC) coupled to the distal portion of the flexible elongate member, wherein the ASIC is electrically coupled to the PMUT. In some instances, the ASIC includes: a pulser for driving the PMUT, an amplifier for receiving and amplifying signals representative of ultrasound echoes received by the PMUT, a protection circuit configured to prevent the amplifier from being damaged by high voltage transmit pulses from the pulser and allow the amplifier to receive the low amplitude echo signals from the PMUT, and timing and control circuitry for coordinating operation of the pulser, amplifier, and protection circuit.

In some instances, the rotational IVUS device further comprises a four-lead electrical cable, wherein a distal portion of the four-lead electrical cable is electrically coupled to the ASIC. A proximal portion of the four-lead electrical cable is coupled to a connector configured to connect the four-lead electrical cable to a patient interface module (PIM) in some embodiments. In some arrangements, the four-lead electrical cable is shielded. Further, in some instances, the four-lead electrical cable is arranged to include two pairs of balanced signal leads. In that regard, each of the balanced signal lead pairs operates in a differential mode in some implementations. In some embodiments, each pair of balanced signal leads consists of a diagonally opposed pair of conductors such that the four-lead electrical cable is arranged in a star quad configuration. In some instances, the rotational IVUS device further comprises a three-lead, shielded electrical cable, wherein a distal portion of the three-lead, shielded electrical cable is electrically coupled to the ASIC such that a pair of the three leads form a balanced transmission line and the remaining lead and the shield form an unbalanced transmission line.

In some instances, the PMUT is formed on a microelectromechanical system (MEMS) component. In that regard, the ASIC is flip-chip bonded to the MEMS component, wire bonded to the MEMS component, and/or integrally formed with the MEMS component in some embodiments. In some implementations, the MEMS component and the ASIC are electrically coupled to a flex circuit substrate.

In another embodiment, a rotational intravascular ultrasound (IVUS) system is provided. The system includes an imaging device, an interface module configured to connect with a proximal connector of the imaging device; and an intravascular ultrasound (IVUS) processing component in communication with the interface module. In some instances, the imaging device of the system comprises: a flexible elongate member having a proximal portion and a distal portion; a proximal connector coupled to the proximal portion of the flexible elongate member; a piezoelectric micromachined ultrasound transducer (PMUT) coupled to the distal portion of the flexible elongate member; and an application-specific integrated circuit (ASIC) coupled to the distal portion of the flexible elongate member, wherein the ASIC is electrically coupled to the PMUT. In that regard, the ASIC includes a pulser for driving the PMUT, an amplifier for receiving and amplifying signals representative of ultrasound echoes received by the PMUT, a protection circuit configured to prevent the amplifier from being damaged by high voltage transmit pulses from the pulser and allow the amplifier to receive the low amplitude echo signals from the PMUT, and timing and control circuitry for coordinating operation of the pulser, amplifier, and protection circuit.

In another embodiment, a method of forming a rotational intravascular imaging device is provided. The method includes: providing a piezoelectric micromachined ultrasound transducer (PMUT) coupled to the distal portion of the flexible elongate member; providing an application-specific integrated circuit (ASIC); electrically coupling the PMUT and the ASIC; and securing the PMUT and the ASIC to a distal portion of a flexible elongate member sized and shaped for insertion into human vasculature. In some instances, the ASIC includes: a pulser for driving the PMUT, an amplifier for receiving and amplifying signals representative of ultrasound echoes received by the PMUT, a protection circuit configured to prevent the amplifier from being damaged by high voltage transmit pulses from the pulser and allow the amplifier to receive the low amplitude echo signals from the PMUT, and timing and control circuitry for coordinating operation of the pulser, amplifier, and protection circuit. In some instances, the provided PMUT is formed on a microelectromechanical system (MEMS) component.

Some embodiments of the present disclosure establish a circuit architecture that provides the needed signal amplification and an efficient pulser circuit, with an electrical interface that requires a small number of electrical leads. In that regard, a smaller number of leads allows larger diameter conductors to be used within the limited space of the flexible elongate member, resulting in reduced cable attenuation and low electrical loss in the interconnect cable extending along the length of the flexible elongate member. Further, embodiments of the present disclosure provide excellent cable impedance matching. In that regard, a four-lead interface facilitates a cable design consisting of a pair of balanced transmission lines, with each transmission line properly terminated to minimize reflections and distortion of the frequency response that can cause artifacts or degradation in the image. Alternatively, a four-lead interface facilitates an alternative cable design (shielded twisted triplet) consisting of a one balanced transmission line, properly terminated to minimize reflections and distortion of the frequency response that can cause artifacts or degradation in the image, while the high voltage DC and ground signals are carried by an unbalanced conductor pair, where impedance matching and balance are not important.

Further, embodiments of the present disclosure also provide low signal coupling. For example, the four-lead cable can be operated in a "star quad" configuration with diagonal conductor pairs forming independent transmission lines. In this configuration, coupling between diagonal signal pairs, each operated in differential mode, is minimized by the symmetry of the coupling to provide low cross-talk between the multiple signals carried by the cable. Also, a shielded twisted triplet cable can be operated in a configuration with two of the three twisted conductors forming a balanced transmission line, while the third twisted conductor and the shield carry the high voltage DC and ground signals. In this configuration, coupling between the balanced signal pair operated in differential mode and the other conductors is minimized by symmetry.

Further still, embodiments of the present disclosure provide low electromagnetic interference (EMI). In that regard, the four-lead interface facilitates a cable design consisting of a pair of balanced transmission lines. The balanced design inhibits radiation of EMI, as well as reducing the susceptibility of the system to external interference from other devices. The four-lead interface cable is jacketed with an electrical shield conductor in some instances to further suppress EMI and susceptibility to external interference. Also, a four-lead interface facilitates a cable design consisting of a shielded twisted triplet, comprised of one balanced signal pair and one unbalanced pair. This balanced design inhibits radiation of EMI, as well as reduces the susceptibility to external interference from other devices, while the unbalanced pair carries only low frequency signals, not prone to generating EMI. The shielded twisted triplet cable design includes an electrical shield conductor to further suppress EMI and susceptibility to external interference.

Embodiments of the present disclosure also provide design flexibility, small integrated circuit die dimensions suitable for use in intravascular catheters and/or guidewires, low power dissipation, high transmit voltages, and an efficient protection circuit. For example, the use of a serial communication scheme makes it feasible to add flexibility and advanced features to the circuit design without complicating the four-lead physical interface between the PIM and the transducer. The circuit described herein is implemented in a compact application-specific integrated circuit (ASIC) and the four lead electrical interface consumes only a small portion of the device area such that the system can be implemented in catheters and guidewires having an outer diameter as small as 0.020" (0.5 mm) in some embodiments. Embodiments of the circuits described herein are designed to minimize power dissipation to avoid excessive temperature rise at the distal end of the catheter. Also, embodiments of the circuits described herein include a high voltage pulser at the distal end of the catheter that avoids the significant cable losses associated with a PIM-based pulser circuit. This approach also reduces the EMI that might otherwise be produced by sending a high voltage transmit pulse through the electrical cable extending along the length of the device, connecting the PIM to the transducer. Further, embodiments of the circuits described herein implement an efficient protection circuit using an actively controlled analog switch to isolate the sensitive amplifier inputs from the high voltage transmit pulse applied to the transducer. This analog switch based protection circuit design is facilitated by the proximity between the transmitter, amplifier, protection, and timing circuits, all of which are integrated into a single ASIC.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

To advance the performance of rotational IVUS imaging catheters compared to the current state of the art, embodiments of the present disclosure implement a transducer with a broader bandwidth compared to that of the traditional IVUS transducers and incorporate focusing into the transducer as well. The piezoelectric micromachined ultrasound transducer (PMUT) fabricated on a microelectromechanical system (MEMS) substrate using a polymer piezoelectric material, for example as disclosed in U.S. Pat. No. 6,641,540, which is hereby incorporated by reference in its entirety, offers wide bandwidth (>100%) and a spherically-focused aperture. The broad bandwidth is important for producing a short ultrasound pulse to achieve optimum resolution in the radial direction, while the spherically-focused aperture provides optimum resolution in the lateral and elevation dimensions. The improved resolution provided by this advanced ultrasound transducer design facilitates better diagnostic accuracy, enhances the ability to discern different tissue types, and enhances the ability to accurately ascertain the borders of the vessel lumen.

Some embodiments of the present disclosure are directed to a circuit architecture and electrical interface that is particularly well-suited for connecting a polymer-based PMUT to a rotational IVUS imaging system. While polymer PMUT technology offers many advantages, the electrical impedance of a transducer is too high to efficiently drive the electrical cable that connects the transducer at the tip of the IVUS catheter to the IVUS imaging system by way of the patient interface module (PIM). In that regard, the length of the electrical cable can range from about 120 cm to about 200 cm in some instances. Furthermore, the transmit efficiency of polymer piezoelectric material is much lower than that of the traditional lead-zirconate-titanate (PZT) piezoelectric ceramic transducer. Therefore, the signal-to-noise ratio will be compromised unless the deficiency in acoustic output can be compensated by the improved transmit electronics and/or other signal processing advances of the present disclosure.

The embodiments of the present disclosure are motivated by the need for the active electronics to be closely integrated with the polymer PMUT, but this novel concept goes beyond simply adding an amplifier circuit to buffer the echo signal from the high impedance transducer element for transmission over a low impedance electrical cable. In that regard, embodiments of the present disclosure provide the following features: sufficient amplification and other characteristics to efficiently drive the transmission line (electrical cable) connecting the transducer near the catheter's distal end to the PIM connected to the proximal end of the catheter; an active protection circuit with low series impedance and low parasitic shunt capacitance to reliably isolate the sensitive amplifier inputs from the high voltage transmit pulse without dampening the low amplitude echo signal generated by the transducer; a high voltage pulser circuit to generate a transmit waveform sufficient to produce a high acoustic output from the relatively inefficient polymer piezoelectric transducer; a compact electrical interface to the PIM that uses a small number of electrical leads and that minimizes undesirable artifacts such as EMI generation/susceptibility, degraded frequency response for the received echo signals, and/or cable reflections that might distort the transmit trigger pulses and/or interfere with serial data communications; flexible control options to optimize the circuit performance for particular imaging conditions and/or applications; low power dissipation to avoid excessive heat generation at the catheter's distal end; and small size, for compatibility with small flexible rotational IVUS designs.

As noted above, the piezoelectric material used in the polymer PMUT is an inefficient ultrasound transmitter compared to the traditional piezoceramic alternatives. However, the copolymer of vinylidene difluoride with trifluoroethylene, designated p(VDF-TrFE) and typically used for polymer PMUT devices is an effective receiver for ultrasound echo signals in the body, partially attributable to its relatively close match to the acoustic impedance of body tissues. However, the typical polymer PMUT suitable for IVUS imaging has a relatively high electrical impedance of approximately 4 k$\Omega$, corresponding to its low capacitance (<1 pF) and a center frequency of ~40 MHz commonly used for IVUS imaging. Such a high impedance transducer is not suitable for driving the low impedance transmission line (with characteristic impedance in the range of 50$\Omega$ to 100$\Omega$) used to carry the echo signals from the tip of the catheter back to the patient interface module (PIM) where the catheter is connected to the IVUS imaging system. Furthermore, due to the low capacitance of the transducer element, the echo signals will be severely attenuated by any parasitic shunt capacitances on the order of 1 pF or greater.

To overcome these issues related to driving a low impedance transmission line and providing immunity to parasitic capacitance, an amplifier stage is provided in close proximity to the transducer. In some embodiments, the amplifier stage has a high input impedance, on the order of the transducer impedance or greater at the IVUS operating frequency (typically about 40 MHz, but may be in the range from 10 MHz to 100 MHz). The output impedance of the amplifier is ideally matched to the characteristic impedance of the transmission line that will carry the amplified echo signal back to the PIM. The voltage gain for this first stage of amplification does not need to be particularly high, since the polymer PMUT is capable of generating a significant voltage when driving a high impedance (such as the amplifier input). However, even with a voltage gain as low as 1, the amplifier provides significant power gain (~16 dB) as it transforms the transducer impedance of ~4 k$\Omega$ down to the ~100$\Omega$ characteristic impedance of the transmission line. In some embodiments, any additional gain required by the IVUS imaging system, including time-varying gain, is supplied by the PIM.

To isolate the sensitive amplifier inputs from the high voltage transmit pulse used to excite the transducer, a protection circuit is provided for the amplifier circuit that is attached in close proximity to the transducer in some instances. The protection circuit blocks the high voltage transmit pulse (~100V) from reaching the amplifier inputs, but it allows the low amplitude echo signals (typically 1V or less) to reach the amplifier inputs with minimal loss attributable to the combination of series resistance and shunt capacitance of the protection circuit. Some ultrasound imaging systems use a passive network for the protection circuit, including resistors, capacitors, and inductors, combined with nonlinear elements (usually diodes) to implement the required protection features. This sort of passive protection circuit typically requires significant compromises that are particularly troublesome in the context of the low capacitance polymer PMUT. In addition, the passive elements required for the protection circuit are often bulky and difficult to integrate on the tiny ASIC that is to be attached in close proximity to the transducer at the distal end of the imaging device.

Embodiments of the present disclosure implement more elaborate protection schemes that use active elements (e.g., transistors) to implement the protection functions. Such active protection circuits can be more efficient and more readily implemented on an ASIC. One embodiment of an active protection circuit implements a high voltage analog switch circuit that is controlled by a timing circuit to open during the transmit pulse and to close during receiving of the ultrasound echo signals. One of the critical complications associated with this approach is that the timing signal that opens the switch during transmit pulse must be 100% reliable, since a single errant high voltage pulse could destroy the amplifier. This level of reliability is difficult to ensure when the timing, transmitter, and protection circuits are physically separated from one another. Accordingly, in some embodiments of the present disclosure the timing, transmitter, and protection circuits are closely coupled together within a single ASIC.

Integrating a transmitter with the transducer element is rarely considered since the large, high-voltage transistors required for a conventional transmitter circuit are cumbersome if not impossible to include in a catheter tip mounted circuit. Fleischman et al. have developed an integrated amplifier circuit with a passive protection circuit designed for use with a PMUT, however that circuit does not include the integrated transmitter, active protection circuit, or other advanced features of the present disclosure. See, Fleischman, A.; Chandrana, C.; Jin Fan; Talman, J.; Garverick, S.; Lockwood, G.; Roy, S., "Components for focused integrated pMUTs for high-resolution medical imaging," *Ultrasonics Symposium,* 2005 IEEE, vol.2, no., pp. 787-791, 18-21 Sept. 2005. By incorporating the transmitter circuit into the ASIC, closely coupled with the PMUT MEMS in accordance with embodiments of the present disclosure, a number of significant advantages can be realized: high transmit efficiency based on avoiding the losses within the cable connecting the PIM to the transducer—cable losses may be 10 dB or more in a typical rotational IVUS catheter, necessitating a very high transmit voltage at the PIM to achieve the desired pulse amplitude at the transducer; relatively small transistors can be used to implement the pulser circuit if it is only required to drive the small capacitance of the polymer PMUT, and not the large parasitic load represented by the electrical cable and other circuit elements; reduced EMI resulting from transmitting only a low amplitude trigger signal over the cable instead of the more typical high current, high voltage transmit pulse; and facilitation of reliable, efficient, active protection circuit based on a high voltage analog switches, which is difficult to safely implement unless the transmitter and protection circuit are closely coupled to one another.

Previous researchers have considered the problem of supporting active electronics in a rotational IVUS catheter, and various schemes have been proposed using as few as two electrical leads to deliver power and transmit pulses to a catheter-mounted amplifier circuit, and to receive the echo signals over that same two-conductor cable. See, for example, U.S. Pat. No. 6,511,432, which is hereby incorporated by reference in its entirety. However, these schemes involve significant compromise to the circuit design, degrading the performance that can be achieved from an advanced transducer. Embodiments of the present disclosure identify a more optimal four wire electrical interface that offers a wide array of benefits, with minimal compromise to the performance of the circuit and transducer, while maintaining a small cable dimension that can be readily accommodated by a rotational IVUS catheter. One implementation of such an arrangement for the electrical cable uses four conductors, twisted together into a symmetrical quad and treated as two diagonal conductor pairs. In fact, a twisted quad occupies only a slightly larger cylindrical space (20% larger diameter) compared to a twisted pair of the same size conductors.

In such a twisted quad cable embodiment, one diagonal pair of conductors provides a balanced transmission line that serves the following multiple purposes: (1) conducting the balanced signal from the ASIC amplifier output to the PIM amplifier input, (2) carrying the transmit trigger pulses as a balanced differential signal from the PIM transmit trigger circuitry to the transmitter and timing circuitry included on the ASIC, (3) supplying low voltage DC power as the common mode voltage on the conductor pair (referenced to the ground conductor of the second pair), (4) providing receiver timing signals to turn the amplifier circuitry on and off as needed to minimize power dissipation in the ASIC, and (5) creating a serial communication channel to support advanced features such as programmability. The second diagonal pair of conductors carries the high voltage supply and ground. The high voltage/ground pair, besides simply providing those DC voltages, also contributes a significant distributed capacitance that stores energy to be used by the pulser circuit when it delivers a high power transmit pulse to the transducer. In practice, when the transmitter is triggered to generate a high power pulse to the transducer, it also launches a traveling wave as a balanced signal onto the high voltage/ground conductor pair. When the traveling wave reaches the PIM, the PIM supplies the charge needed to replenish what has been drawn from that conductor pair by the transmit pulse. This cable configuration provides all of the required functions, using a four wire interface with all signals transmitted over balanced lines, each terminated with the appropriate characteristic impedance. The balanced, terminated transmission lines provide reduced generation and susceptibility to EMI, low distortion of the transmit waveform, high speed communication, minimal distortion of the amplifier frequency response, and other electrical advantages. In some embodiments, the cable includes an optional shield around the twisted quad to further protect the signal lines from EMI, to reduce electromagnetic interference emitted from the signal lines, and to provide added mechanical integrity.

An alternative cable design according to the present disclosure, offering many of the same advantages described previously in conjunction to the twisted quad configuration, is a shielded, twisted triplet. In this case, two conductors of the twisted triplet serve the multiple functions describe previously for the first pair of conductors of the twisted quad, namely: (1) conducting the balanced ASIC amplifier output to the PIM amplifier input, (2) carrying the transmit trigger pulses as a balanced differential signal from the PIM transmit trigger circuitry to the transmitter and timing circuitry included on the ASIC, (3) supplying low voltage DC power as the common mode voltage on the conductor pair (in this case referenced to the shield, which serves as the ground conductor), (4) providing receiver timing signals to turn the amplifier circuitry on and off as needed to minimize power dissipation in the ASIC, and (5) creating a serial communication channel to support advanced features such as programmability. The ground conductor serves as the shield, while the high voltage is carried by the third conductor of the twisted triplet. Since the shield is symmetrical with respect to the conductors of the twisted triplet, there is minimal differential interference signal coupled from the shield to the balanced signal lines that carry the amplifier output. Likewise, by symmetry, there is minimal coupling of interference on the high voltage conductor into the balance signal lines. Furthermore, there is typically very little high frequency noise on the high voltage signal line, except for a brief transient during and immediately after a transmit pulse. Most of that high frequency transient will have dissipated by the time the earliest echo signals of interest return from the vessel tissue. The shielded twisted triplet is a highly manufacturable configuration, with the triplet forming an inherently stable and symmetrical bundle, and with the shield providing mechanical integrity for the cable and protection from external interference.

Another important aspect of embodiments of the present disclosure is to manage the power dissipation in the circuit to prevent excessive temperature rise at the distal end of the catheter where the ASIC is located. The largest source of power dissipation in the ASIC is the amplifier circuit, which requires a relatively high bias current to provide the desired performance. One method to reduce the power consumption is to shut down the amplifier when it is not needed. Typically, there is a period of approximately 10 μsec after each transmit pulse for receiving ultrasound echoes, and a typical pulse repetition period for transmit pulses is about 60 μsec, resulting in an amplifier duty cycle as low as 16%. By placing the amplifier in a low power standby mode when it is not needed, the power can be reduced to approximately one-sixth of what would be required for continuous operation. One option for controlling the amplifier shutdown is to include a timing circuit on the ASIC to enable the amplifier for a 10 μsec duration after each transmit pulse. While this approach is simple to implement and suitable for some applications, it lacks the flexibility to adapt to different transducer configurations or imaging modes that might demand a different receive duration. An alternative approach is to define a command protocol whereby one pulse sequence sent from the PIM to the ASIC triggers a transmit pulse, while a later pulse sequence triggers the termination of the receive window. In this fashion, the PIM can control the ASIC timing and the PIM can be easily programmed and/or reprogrammed to adjust the timing for each mode or transducer configuration. One example of a simple protocol is defined as follows: the first pulse sequence to be sent from the PIM after a long quiet spell (20 μsec, for example) would be interpreted as a transmit pulse sequence, and any subsequent pulse occurring within a 20 μsec window would be interpreted as terminating the receive window and rearming the transmitter to fire on the next pulse sequence. As one skilled in the art will appreciate, any number of various timing protocols may be utilized, depending on the particular transducer configuration and/or imaging mode.

The ability to manage the circuit power dissipation by controlling the amplifier duty cycle with a simple sequence of pulses as described previously adds flexibility to the system to address multiple applications. For greater flexibility, it may be desirable to add a higher degree of programmability to the ASIC, to enable a wider range of programmability in the circuit operation. This can be accomplished without greatly increasing the complexity of the device by defining a simple serial communication protocol to permit the PIM to send configuration information to the ASIC over the same two-wire communication link as used for the transmit trigger pulses and for optional receive window termination pulses. Examples of the type of configuration information that might be programmed into the circuit over the serial communications link include amplifier gain, amplifier bias current, transmit damping pulse duration, and/or other parameters.

Figure 1:
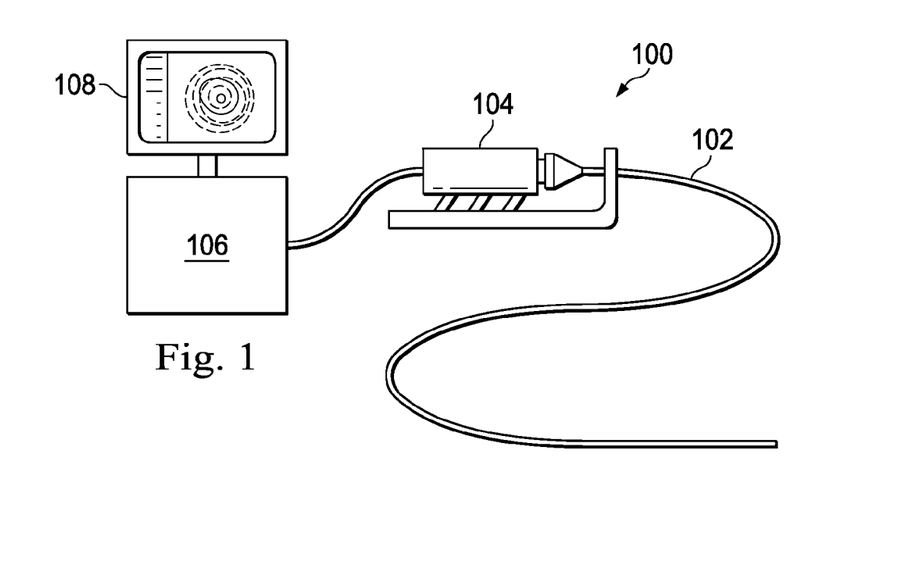
FIG. 1 is a diagrammatic schematic view of an imaging system according to an embodiment of the present disclosure.

Referring to FIG. 1, shown therein is an IVUS imaging system 100 according to an embodiment of the present disclosure. In some embodiments of the present disclosure, the IVUS imaging system 100 is a PMUT rotational IVUS imaging system. In that regard, the main components of the PMUT rotational IVUS imaging system are the PMUT rotational IVUS catheter 102, a PMUT catheter compatible patient interface module (PIM) 104, an IVUS console or processing system 106, and a monitor 108 to display the IVUS images generated by the IVUS console 106. Some of the aspects of the present disclosure that distinguish this PMUT IVUS imaging system 100 from a traditional rotational IVUS imaging system include the PMUT catheter 102 and the PMUT-compatible PIM 104 that implements the appropriate interface specifications to support the PMUT catheter 102. As discussed in greater detail below, the PMUT rotational IVUS catheter 102 includes a PMUT ultrasound transducer along with its associated circuitry mounted near a distal tip of the catheter, a four conductor electrical cable, and the appropriate electrical connector to support the rotational interface. The PMUT-compatible PIM 104 generates the required sequence of transmit trigger signals and control waveforms to regulate the operation of the circuit and processes the amplified echo signals received over that same conductor pair. The PMUT-compatible PIM 104 also supplies the high- and low-voltage DC power supplies to support operation of the PMUT rotational IVUS catheter 102. An important feature of the PMUT-compatible PIM 104 is that it must deliver DC supply voltages to the PMUT circuitry of the catheter 102 across a rotational interface. This requirement largely precludes the option of a rotary transformer, commonly used for traditional rotational IVUS systems, since a transformer can only convey AC signals from the primary to the secondary side. Practical options for delivering DC power across a rotating interface include the use of slip-rings and/or the implementation of the active spinner technology described in U.S. Patent Application Publication No. 2010/0234736, which is hereby incorporated by reference in its entirety.

Figure 2:
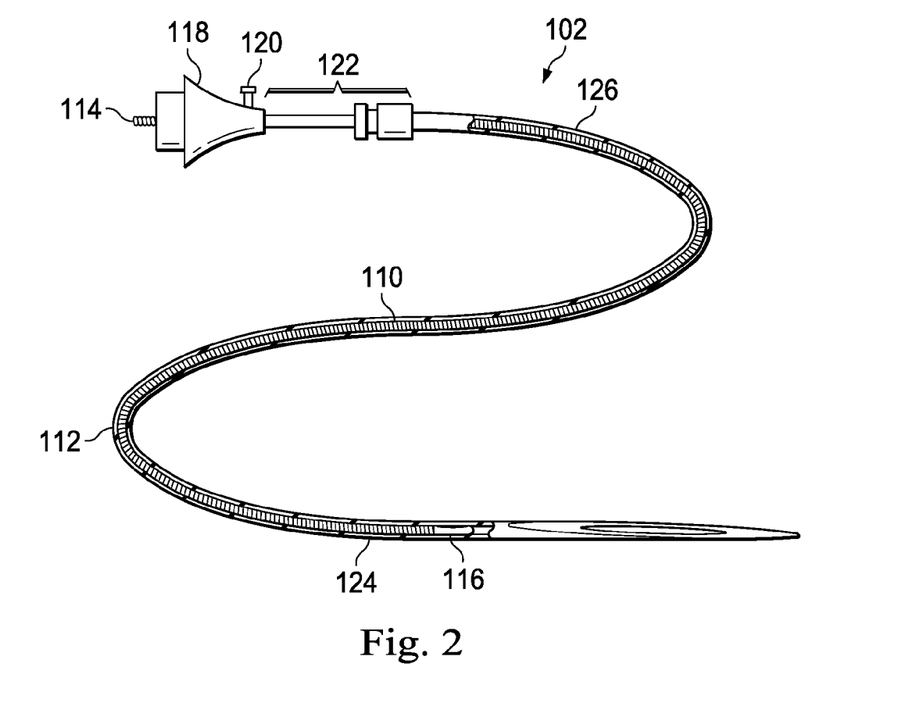
FIG. 2 is a diagrammatic, partial cutaway perspective view of an imaging device according to an embodiment of the present disclosure.

Referring now to FIG. 2, shown therein is a diagrammatic, partial cutaway perspective view of the PMUT catheter 102 according to an embodiment of the present disclosure. In that regard, FIG. 2 shows additional detail regarding the construction of the PMUT rotational IVUS catheter 102. In many respects, this catheter is similar to traditional rotational IVUS catheters, such as the Revolution® catheter available from Volcano Corporation and described in U.S. Pat. No. 8,104, 479, or those disclosed in U.S. Pat. Nos. 5,243,988 and 5,546, 948, each of which is hereby incorporated by reference in its entirety. In that regard, the PMUT rotational IVUS catheter 102 includes an imaging core 110 and an outer catheter/sheath assembly 112. The imaging core 110 includes a flexible drive shaft that is terminated at the proximal end by a rotational interface 114 providing electrical and mechanical coupling to the PIM 104 of FIG. 1. The distal end of the flexible drive shaft of the imaging core 110 is coupled to a transducer housing 116 containing the PMUT and associated circuitry, which are described in greater detail below. The catheter/sheath assembly 112 includes a hub 118 that supports the rotational interface and provides a bearing surface and a fluid seal between the rotating and non-rotating elements of the catheter assembly. The hub 118 includes a luer lock flush port 120 through which saline is injected to flush out the air and fill the inner lumen of the sheath with an ultrasound-compatible fluid at the time of use of the catheter. The saline or other similar flush is typically required since air does not readily conduct ultrasound. Saline also provides a biocompatible lubricant for the rotating driveshaft. The hub 118 is coupled to a telescope 122 that includes nested tubular elements and a sliding fluid seal that permit the catheter/sheath assembly 112 to be lengthened or shortened to facilitate axial movement of the transducer housing within an acoustically transparent window 124 of the distal portion of the catheter 102. In some embodiments, the window 124 is composed of thin-walled plastic tubing fabricated from material(s) that readily conduct ultrasound waves between the transducer and the vessel tissue with minimal attenuation, reflection, or refraction. A proximal shaft 126 of the catheter/sheath assembly 112 bridges the segment between the telescope 122 and the window 124, and is composed of a material or composite that provides a lubricious internal lumen and optimum stiffness, but without the need to conduct ultrasound.

Figure 3:
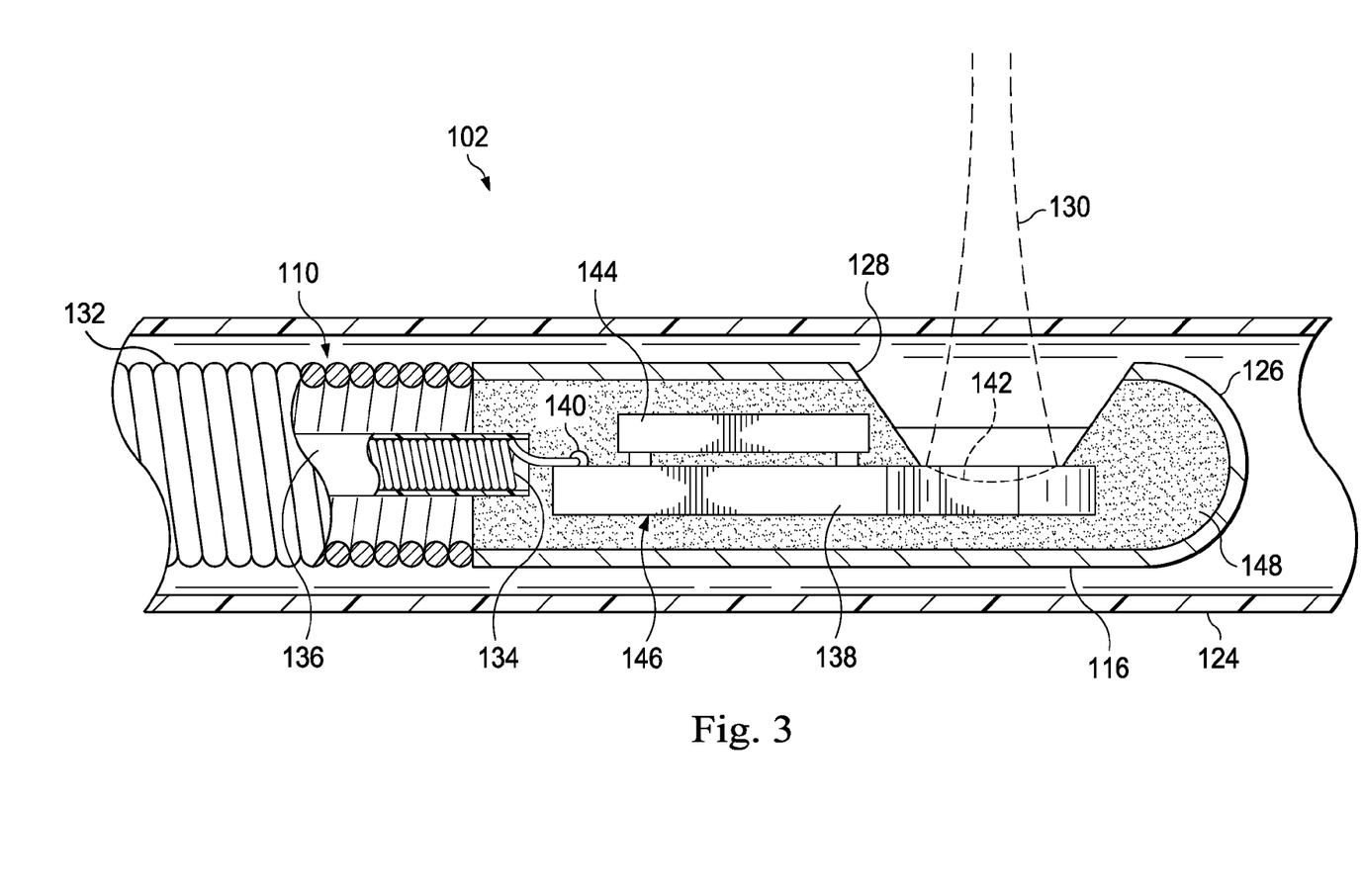
FIG. 3 is a diagrammatic, cross-sectional side view of a distal portion of the imaging device of FIG. 2.

Referring now to FIG. 3, shown therein is a cross-sectional side view of a distal portion of the catheter 102 according to an embodiment of the present disclosure. In particular, FIG. 3 shows an expanded view of aspects of the distal portion of the imaging core 110. In this exemplary embodiment, the imaging core 110 is terminated at its distal tip by a housing 116 fabricated from stainless steel and provided with a rounded nose 126 and a cutout 128 for the ultrasound beam 130 to emerge from the housing 116. In some embodiments, the flexible driveshaft 132 of the imaging core 110 is composed of two or more layers of counter wound stainless steel wires, welded, or otherwise secured to the housing 116 such that rotation of the flexible driveshaft also imparts rotation on the housing 116. In the illustrated embodiment, the PMUT MEMS 138 includes a spherically focused transducer 142 and carries an application-specific integrated circuit (ASIC) 144. The ASIC 144 is electrically coupled to the PMUT MEMS 138 through two or more connections. In that regard, in some embodiments of the present disclosure the ASIC 144 includes an amplifier, a transmitter, and a protection circuit associated with the PMUT MEMS as discussed above. In some embodiments, the ASIC 144 is flip-chip mounted to the substrate of the PMUT MEMS 138 using anisotropic conductive adhesive or suitable alternative chip-to-chip bonding method. When assembled together the PMUT MEMS 138 and the ASIC 144 form an ASIC/MEMS hybrid assembly 146 that is mounted within the housing 116. An electrical cable 134 with optional shield 136 is attached to the ASIC/MEMS hybrid assembly 146 with solder 140. The electrical cable 134 extends through an inner lumen of the flexible driveshaft 132 to the proximal end of the imaging core 110 where it is terminated to the electrical connector portion of the rotational interface 114 shown in FIG. 2. In the illustrated embodiment, the ASIC/MEMS hybrid assembly 146 is secured in place relative to the housing 116 by an epoxy 148 or other bonding agent. The epoxy 148 also serves as an acoustic backing material to absorb acoustic reverberations propagating within the housing 116 and as a strain relief for the electrical cable 134 where it is soldered to the ASIC/MEMS hybrid assembly 146.

Figure 4:
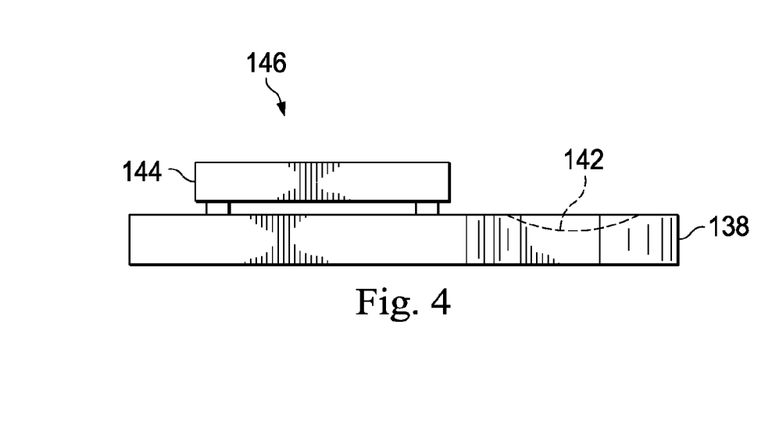
FIG. 4 is a diagrammatic side view of components of the distal portion of the imaging device shown in FIG. 3, including a MEMS component and an ASIC component, according to an embodiment of the present disclosure.
Figure 5:
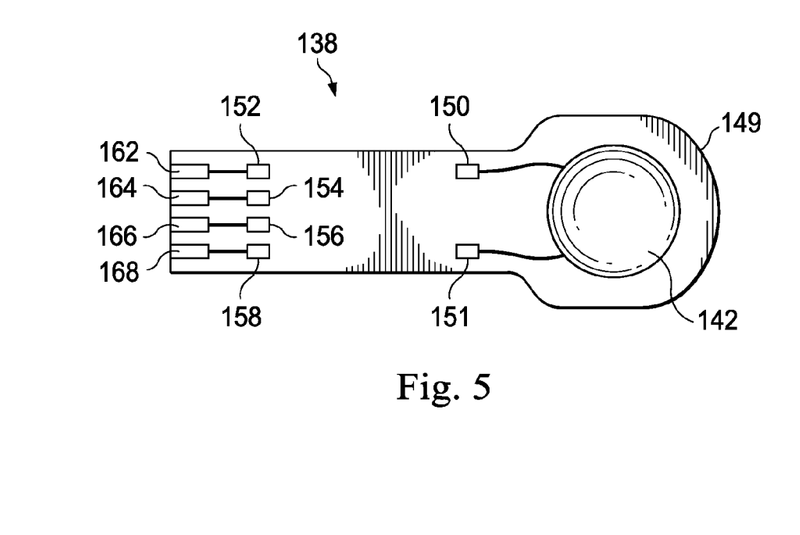
FIG. 5 is a diagrammatic bottom view of the ASIC component of the components illustrated FIG. 4.
Figure 6:
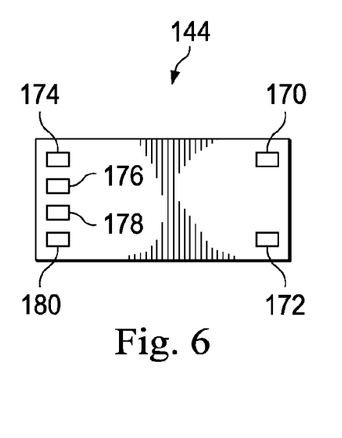
FIG. 6 is a diagrammatic top view of the MEMS component of the components illustrated in FIG. 4.

Referring now to FIGS. 4-6, shown therein are additional aspects of the PMUT MEMS component 138 and ASIC 144 that form the ASIC/MEMS hybrid assembly 146. The MEMS component 138 in the embodiment of FIGS. 4-6 is a paddle-shaped silicon component with the piezoelectric polymer transducer 142 located in the widened portion 149 of the substrate located at the distal end of the MEMS component 138. The narrow portion of the substrate positioned proximal of the widened portion 149 is where the ASIC 144 is mounted to the MEMS component 138. In that regard, the MEMS component 138 includes ten bond pads, with bond pads 150, 151, 152, 154, 156, and 158 of the MEMS 138 configured to match up respectively with six bond pads 172, 170, 180, 178, 176, and 174 on the ASIC 144 (shown in FIG. 6) when the ASIC is flip-chip mounted onto the MEMS 138. The flip-chip mounting is accomplished using anisotropic conductive adhesive, gold-to-gold thermosonic bonding, and/or other suitable method. Solder reflow is not convenient for this application in some instances, since the copolymer transducer element is subject to depoling at temperatures as low as 100° C., well below conventional soldering temperatures. Anisotropic conductive adhesive can be cured at temperatures below 100° C., as long as the cure time is increased to account for the low cure temperature. In this embodiment, the bond pads 152, 154, 156, and 158 are coupled to bond pads 162, 164, 166, and 168 by conductive traces included on the MEMS substrate, with the bond pads 162, 164, 166, and 168 serving as terminations for the four conductors of the electrical cable 134, shown in FIG. 3. In that regard, the four conductors of the electrical cable 134 are soldered or otherwise fixedly attached to bond pads 162, 164, 166, and 168, which are electrically coupled with the bond pads 152, 154, 156, and 158. In other embodiments, the four conductors of the electrical cable 134 are soldered or otherwise fixedly attached directly to the ASIC bond pads 174, 176, 178, and 180.

Figure 7:
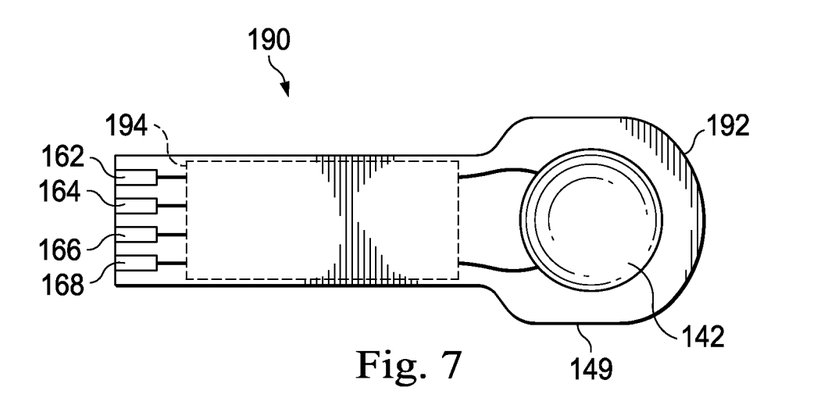
FIG. 7 is a diagrammatic top view of a monolithic ASIC/MEMS component, combining analogous features to the MEMS and ASIC components shown in FIGS. 5 and 6, illustrating an alternative embodiment of the present disclosure.
Figure 8:
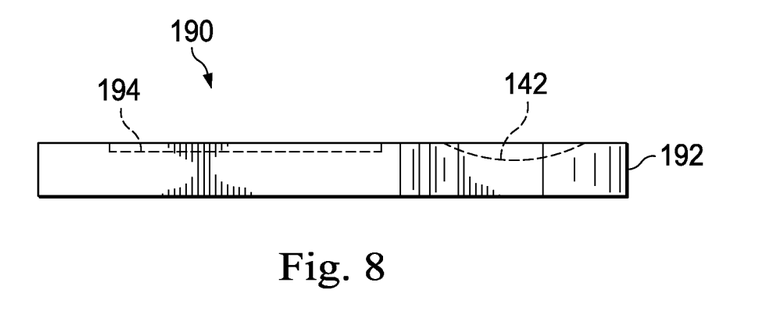
FIG. 8 is a diagrammatic partial cross-sectional side view of the ASIC/MEMS component illustrated in FIG. 7.

Referring now to FIGS. 7 and 8, shown therein is an ASIC/MEMS assembly 190 according to another embodiment of the present disclosure. In that regard, the ASIC/MEMS assembly 190 is configured for positioning within a distal portion of an imaging core, such as imaging core 110 described above. The ASIC/MEMS assembly 190 is a monolithic structure comprising a MEMS substrate 192 with an ASIC 194 embedded therein. In that regard, the ASIC/MEMS assembly 190 includes features and functionality similar to those discussed above with respect to ASIC/MEMS hybrid assembly 146. Accordingly, the same reference numerals have been utilized to refer to analogous features. However, in the exemplary configuration of FIGS. 7 and 8, the ASIC 194 and MEMS 192 are fabricated on the same silicon wafer to produce a monolithic device. In that regard, the MEMS processes used to produce the PMUT structure are compatible with the CMOS processes used to produce the ASIC. Accordingly, in some instances the ASIC circuitry is first fabricated on a wafer and then that same wafer is processed through the MEMS foundry to add the transducer structures. The resultant monolithic structure consists of a paddle-shaped MEMS 192 with the transducer 142 located in the widened portion 149 of the substrate with the ASIC 194 embedded in the narrow portion of the substrate that extends proximal of the widened portion. This monolithic approach for assembly 190 produces a simpler mechanical structure and eliminates the need for flip-chip bonding of the ASIC and MEMS components. However, the monolithic approach adds complexity to the manufacturing process since both the ASIC and MEMS features and related processing techniques must coexist on a single wafer without interfering with one other. Furthermore, as will be illustrated subsequently, it may be advantageous to separate the electronic circuitry (ASIC) from the transducer (MEMS) to simplify the assembly process or to facilitate mounting the transducer at the appropriate angle to enable Doppler color flow imaging.

Figure 9:
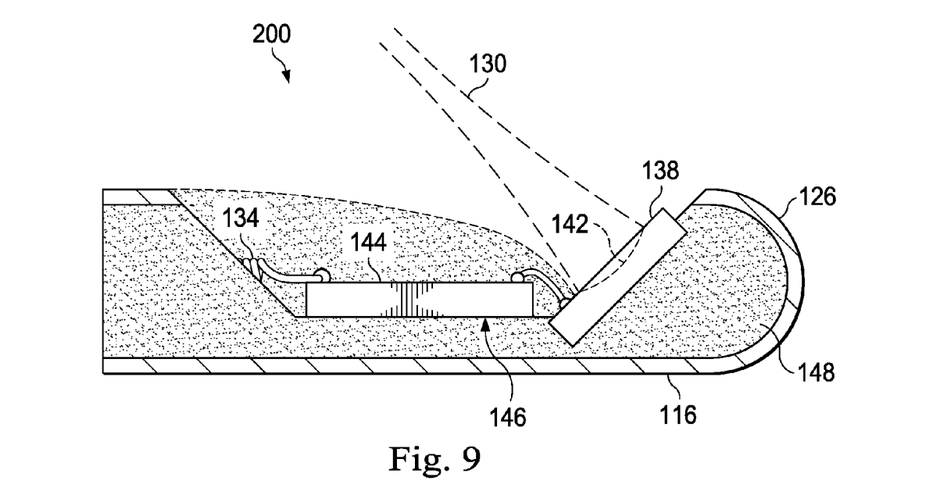
FIG. 9 is a diagrammatic, cross-sectional side view of a distal portion of an imaging device according to another embodiment of the present disclosure.

Referring now to FIG. 9, shown therein is a cross-sectional side view of a distal portion of an imaging core 200 according to another embodiment of the present disclosure. The imaging core 200 may be similar to the imaging core 110 of catheter 102 described above. In that regard, the imaging core 200 includes features and functionality similar to those discussed above with respect to imaging core 110. Accordingly, the same reference numerals have been utilized to refer to analogous features. For example, the imaging core 200 includes a MEMS 138 having a transducer 142 formed thereon and an ASIC 144 electrically coupled to the MEMS 138. However, in the exemplary configuration of FIG. 9, the ASIC 144 and the MEMS 138 components are wire-bonded together, mounted to the transducer housing 116, and secured in place with epoxy 148 or other bonding agent to form an ASIC/MEMS hybrid assembly 146. The leads of the cable 134 are soldered or otherwise electrically coupled directly to the ASIC 144 in this embodiment. In some embodiments of this configuration, the MEMS component 138 is a truncated version of the paddle-shaped device shown in FIGS. 4 and 5, with the narrow "handle" portion of the paddle removed. One advantage of the wire-bonding approach is that the MEMS component carrying the transducer 133 can be mounted at an oblique angle with respect to the longitudinal axis of the housing 116 and imaging core 200 such that the ultrasound beam 130 propagates at an oblique angle with respect to a perpendicular to the central longitudinal axis of the imaging core. This tilt angle helps to diminish the sheath echoes that can reverberate in the space between the transducer and the catheter sheath 112, and it also facilitates Doppler color flow imaging as disclosed in U.S. Provisional Patent Application No. 61/646,080 titled "DEVICE AND SYSTEM FOR IMAGING AND BLOOD FLOW VELOCITY MEASUREMENT" and U.S. Patent Application No. 61/646,074 titled "ULTRASOUND CATHETER FOR IMAGING AND BLOOD FLOW MEASUREMENT IN A VESSEL", each of which is hereby incorporated by reference in its entirety.

Figure 10:
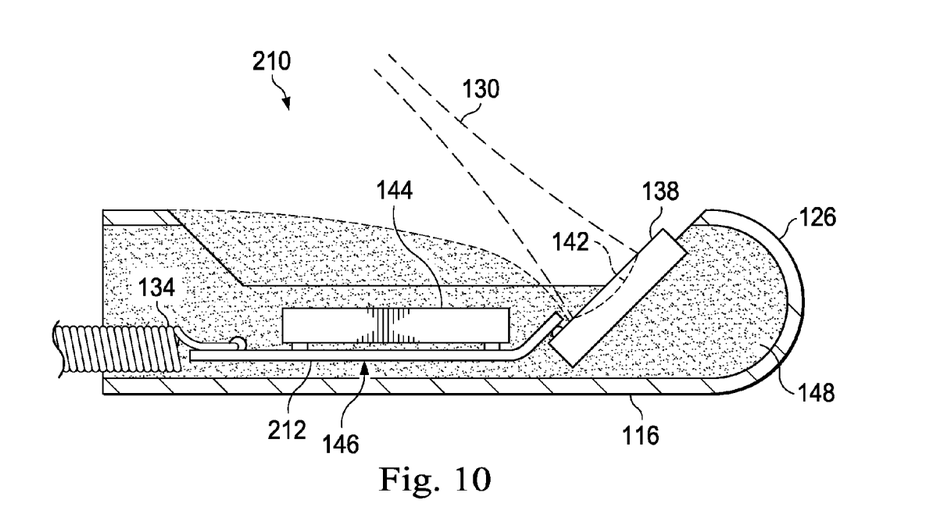
FIG. 10 is a diagrammatic, cross-sectional side view of a distal portion of an imaging device similar to that of FIG. 9, but illustrating another embodiment of the present disclosure.

Referring now to FIG. 10, shown therein is a cross-sectional side view of a distal portion of an imaging core 210 according to another embodiment of the present disclosure. The imaging core 210 may be similar to the imaging core 110 of catheter 102 and/or imaging core 200 described above. In that regard, the imaging core 210 includes features and functionality similar to those discussed above with respect to imaging core 110 and imaging core 200. Accordingly, the same reference numerals have again been utilized to refer to analogous features. In the exemplary configuration of FIG. 10, the ASIC 144 and MEMS 138 are mounted together on a flex circuit substrate 212 to form an ASIC/MEMS hybrid assembly 146, which is then mounted in the housing 116 and secured in place with epoxy 148 or other bonding agent. Each of the electrical cable 134, the ASIC 144, and the MEMS 138 are soldered, bonded, and/or otherwise electrically coupled to the flex circuit substrate 212 such that conductors within the flex circuit 212 carry signals among the conductors of the electrical cable 134, the ASIC 144, and the MEMS 138 to facilitate operation of the imaging core 210. For this configuration, the MEMS component 138 is preferably a truncated version of the paddle-shaped device shown in FIGS. 4 and 5, with the narrow "handle" portion of the paddle removed. This flex circuit approach shares the same advantage of the wire-bonded approach of FIG. 9 in allowing the MEMS component 138 carrying the transducer 142 to be mounted at an oblique angle, such that the ultrasound beam 130 propagates at an oblique angle with respect to a perpendicular to the central longitudinal axis of the imaging core. This tilt angle helps to diminish the sheath echoes that can reverberate in the space between the transducer and the catheter sheath 112, and it also facilitates Doppler color flow imaging as described above.

Figure 11:
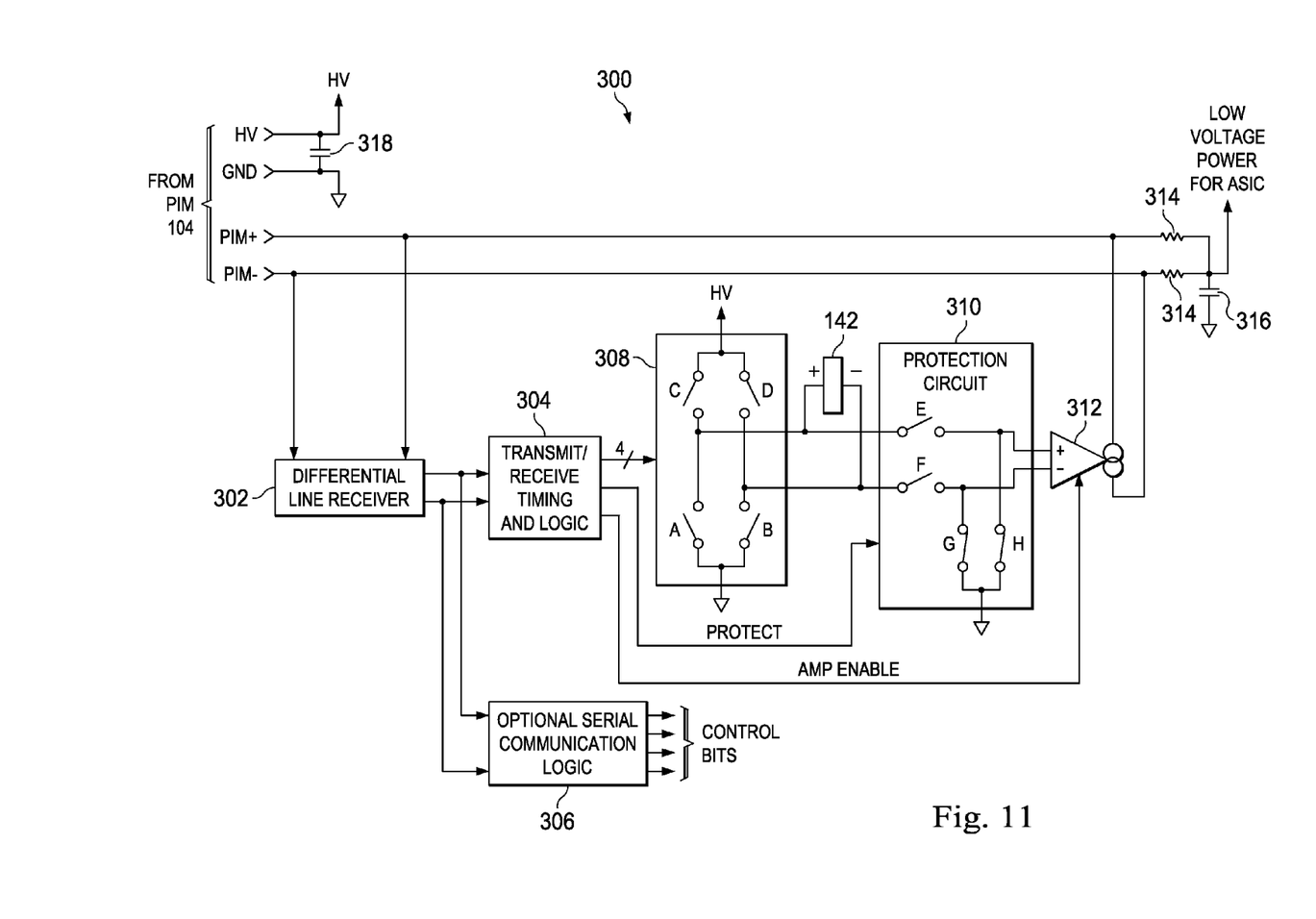
FIG. 11 is a diagrammatic schematic view of a detailed circuit architecture according to an embodiment of the present disclosure.

Referring now to FIG. 11, shown therein is a block diagram 300 of an ASIC configuration according to an embodiment of the present disclosure. In that regard, the ASIC configuration of FIG. 11 is suitable for use as the ASIC 144 described in the above embodiments. As shown, the circuit architecture uses a four wire interface to the PIM 104, comprising four signals designated PIM+, PIM−, HV (high voltage), and GND (ground). There are two leads connecting the circuit to the PMUT 142. The major components of the ASIC are a differential line receiver 302, a transmit/receive timing and logic block 304, an optional serial communication logic block 306, a pulser circuit 308, a protection circuit 310, and an amplifier 312.

The PIM+/− conductor pair serves the multiple functions of: (1) carrying the transmit trigger pulses as a balanced differential signal from the PIM to activate the transmitter and timing circuitry included on the ASIC, (2) conducting the balanced output signal from the amplifier output of the ASIC back to the PIM, (3) supplying low voltage DC power as the common mode voltage on the conductor pair as referenced to the ground conductor, (4) providing receiver timing signals to turn the amplifier circuitry on and off as needed to minimize power dissipation in the ASIC, and (5) creating a serial communication channel to support advanced features such as programmability. The PIM+/− conductor pair is carried by a balanced transmission line that is terminated on the ASIC by a pair of resistors 314 that form a balanced differential termination to minimize cable reflections and distortion of the signals propagating over the transmission line. Typically, the total differential resistance matches the characteristic impedance of the transmission line, such as 75Ω. However, the transmission line will have larger or smaller resistances in some embodiments. The PIM+/− conductor pair carries various digital signals from the PIM to the ASIC in the form of a balanced differential signal pair. In some embodiments, the differential amplitude of the signals is ~9$V_{P-P}$ at the ASIC. This differential signal pair represents three possible states: positive (PIM+=high, PIM−=low), negative (PIM+=low, PIM−=high), or idle (both PIM+ and PIM− nominally equal to the common mode voltage). These digital signals may represent a transmit trigger pulse sequence to activate the pulser circuit 308, a receive window termination pulse to switch the amplifier 312 into a low power state, and/or a serial communication code to configure the circuit or activate various advanced features that might be incorporated in the circuit as discussed above. During the idle state, the buffered echo signal at the amplifier output can be carried over the differential pair as a low-level signal with a differential amplitude typically no greater than 1$V_{P-P}$. In some instances, the common mode voltage of the PIM+/− conductor pair is taken from the midpoint of the differential termination resistance and used to provide a low voltage power supply for the chip. The low voltage power supply is filtered by a capacitor 316 on the order of 100 pF. Since all of the signals carried by the PIM+/− conductor pair are balanced differential signals, there is little ripple in the supply voltage. Furthermore, since the low voltage supply current is low (<1 mA in some instances, excluding the amplifier output current that passes directly from the PIM+/− lines into the amplifier output transistors without passing through the termination resistors), there is minimal voltage drop across the termination resistors (or the resistance of the cable conductors).

The HV signal line carries a high voltage DC supply to the ASIC, typically in the range of 40V to 200V, to power the transmit circuitry 308, which is formed as an H-bridge in the illustrated embodiment. There is a small high voltage filter capacitor 318 (for example, between about 5 pF and about 25 pF, approximately 10 pF in some specific embodiments) included on the ASIC. It is difficult to include a large high voltage capacitor, for example greater than 25 pF, on the ASIC, since such a capacitor would occupy a very large area of an ASIC that must be sized for use within an intravascular imaging device. However, the distributed cable capacitance, on the order of 200 pF for a 160 cm cable length, provides a significant supplement to the on-chip capacitor, helping to stabilize the high voltage supply.

The differential line receiver 302 translates the differential PIM+/− signal representing one of three states (positive, negative, or idle) into a pair CMOS logic levels at the output of the line receiver. In one embodiment, the positive state is represented by a high and a low, the negative state is represented by a low and a high, the idle state is represented by two lows, and the combination of two high levels is an invalid state for the output of the differential line receiver. Alternative combinations of signal levels for positive, negative, and/or idle are utilized in other embodiments. These translated control signals from the PIM 104 are delivered to the transmit/receive timing and logic block 304 and to the optional serial communication logic block 306.

The transmit/receive timing and logic block 304 generates the logic signals to activate the pulser, receiver, and protection circuitry. The H-bridge pulser 308 requires four logic signals to activate the four switches that make up the pulser, and these control signals must cycle the pulser through the appropriate sequence of states, typically high impedance, positive, negative, damping, and finally back to the high impedance state for receiving echo signals. The protection circuit 310 must be carefully coordinated with the pulser operation to ensure that the amplifier 312 is always protected from the high voltage transmit pulses, even during periods of anomalous operation, such as power-on sequencing and other fault conditions. In some embodiments, the amplifier 312 requires a single control signal to enable and disable the amplifier as needed. In some embodiments, the amplifier 312 is the most power-hungry element of the circuit and, therefore, for the lowest power dissipation the amplifier 312 is switched to a low power state when it is not needed as discussed above.

The optional serial communication logic block 306 decodes serial communication sequences on the PIM+/− lines and transforms those sequences into configuration or control data for the ASIC. Configuration bits stored in on-chip registers via these serial commands can activate various optional features of the circuit to optimize its performance for particular product types and/or imaging applications. For example, in some instances configuration bits are used to adjust the gain and/or frequency response of the circuit and/or to modify the transmit/receive timing.

The H-bridge pulser circuit 308 produces a high voltage transmit pulse with a peak-to-peak amplitude approximately twice the high voltage supply. Although there are sixteen possible combinations for activating the four switches that make up the pulser 308, only four of the combinations are used in some embodiments. In such embodiments, the four pulser states are: (1) high-impedance in which all four switches are open to facilitate reception of the low level echo signals on the transducer, (2) positive output with switches B and C closed and A and D open to apply HV to the positive side of the transducer and ground to the negative side, (3) negative output with switches A and D closed and B and C open to apply ground to the positive side of the transducer and high voltage to the negative side, and (4) damping mode with switches A and B closed and C and D open to connect both sides of the transducer to ground. The remaining twelve states represent fault conditions and/or offer no particular benefit.

The protection circuit 310 isolates the sensitive amplifier inputs from the high voltage transmit pulses. The protection circuit 310 consists of one pair of series switches E and F to disconnect the pulser and transducer from the amplifier inputs during the transmit pulse, and a second pair of switches G and H to shunt the amplifier inputs to ground, protecting the amplifier inputs from any signals that leak through the series switches. The protection circuit 310 is preferably activated prior to the transmit pulse and left in that protection mode for a short time after the end of the transmit pulse, to ensure that there are no transients at the start or end of the transmit pulse getting past the protection. A short time after the end of the transmit pulse, the pulser enters the high impedance state, wherein it is effectively isolated from the transducer, and the protection circuit is deactivated, allowing the echo signals from the transducer to reach the amplifier inputs. When the protection circuit is deactivated, the series switches E and F are closed to connect the transducer to the amplifier inputs, and the shunt switches G and H are opened so as not to dampen the amplifier input signals.

The amplifier 312 receives the echo signals from the high impedance (low capacitance) transducer 142 and transforms the impedance to match the characteristic impedance of the PIM+/− transmission line. Typically, the amplifier has a current output stage that provides significant current gain but high output impedance. The effective output impedance of the ASIC is then established by the termination resistors 314. The amplifier 312 may provide voltage gain in addition to the impedance transformation, but the power gain associated with the impedance transformation from the 4 kΩ impedance of a typical PMUT to the 75Ω impedance of the amplifier output already represents a significant power gain of ~17 dB. The protection circuit 310 isolates the amplifier inputs from the high voltage transmit pulses and enables a signal from the transmit/receive logic and timing block 304 to activate the amplifier 312 only during the desired receive window, thereby minimizing the average power dissipation for the amplifier 312, which is typically the largest power drain of the entire circuit.

Figure 12:
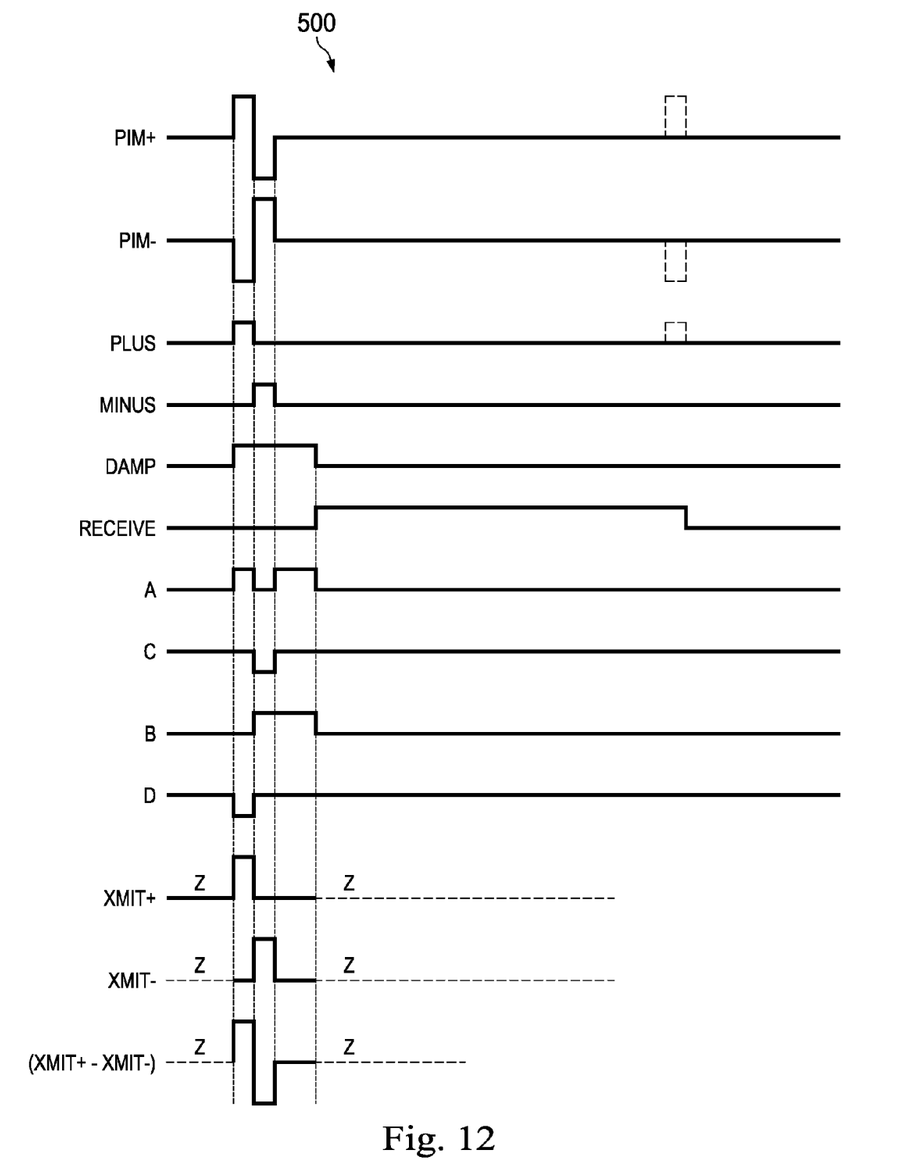
FIG. 12 is a diagrammatic schematic view of timing diagram of a circuit architecture according to an embodiment of the present disclosure.

Referring now to FIG. 12, shown therein is a timing diagram 500 for a circuit architecture according to an embodiment of the present disclosure. In that regard, the timing diagram 500 is suitable for use with embodiments of the present disclosure, including the ASIC configuration of FIG. 11 described above. Accordingly, for the sake of clarity the timing diagram 500 will be discussed in the context of the ASIC configuration of FIG. 11. As shown, a transmit/receive sequence is initiated by a transmit trigger pulse sequence from the PIM, delivered over the PIM+/− differential signal pair. The differential signal is conditioned by the differential line receiver 302 to produce a pair of CMOS signals, PLUS and MINUS for internal use within the ASIC, and representing the three possible states of the PIM+/− differential signal pair (positive, negative, and idle). The leading edge of a PLUS or MINUS pulse triggers the timing signals, DAMP and RECEIVE, and activates the H-bridge pulser 308 to generate a transmit pulse. In some instances, the transmit waveform burst length, polarity, and width are controlled by the transmit trigger pulse sequence delivered over the PIM+/− differential signal pair. In effect, the H-bridge pulser 308 replicates the trigger waveform on the PIM+/− lines, but with a peak-to-peak amplitude that is approximately twice the high voltage power supply. In this illustrative example, the transmit pulse is a single cycle waveform, but it can be a single half-cycle and/or a multiple cycle burst in other embodiments, with the pulse width and burst length adjusted to optimize the transmit spectrum for the desired transducer center frequency and bandwidth. To generate a single cycle transmit waveform, the transmit/receive timing and logic circuitry 304 cycles the pulser 308 through a sequence of states, starting from the high impedance (Z) state, followed by positive, negative, and damping states before returning to the high impedance state at the end of the DAMP timing pulse. At the end of the DAMP pulse, the pulser 308 returns to the high impedance state, and the RECEIVE signal deactivates the protection circuit 310 and enables the amplifier 312 to receive the ultrasound echo signals from the transducer 142 and amplify them for delivery over the PIM+/− lines back to the PIM for further amplification and signal processing by the PIM itself or an IVUS console or processor. The RECEIVE timing signal may be terminated by a one-shot timing circuit within the ASIC, or optionally by a pulse sent over the PIM+/− lines. After termination of the receive window, the amplifier 312 returns to a low power idle state, the protection circuit 310 opens to isolate the amplifier 312 from the pulser 308 and transducer 142, and the pulser 308 remains in the high impedance state awaiting the next transmit trigger pulse.

The circuit architecture and electrical interface described herein is particularly suitable for use with a polymer piezoelectric micromachined ultrasound transducer, and by enabling the use of this advanced transducer technology, it facilitates several important advances in intravascular ultrasound imaging. The polymer PMUT promises high resolution in all three dimensions, thanks to its focused aperture and wide bandwidth, and the embodiments described in the present application overcome the key limitations of such devices, namely: the inability to directly drive a signal over a long transmission line and the low transmit efficiency of the polymer piezoelectric. Further, the circuit architectures that are the subject of the present disclosure provide a buffer amplifier immediately adjacent to the transducer to ensure efficient delivery of the received ultrasound echo signal from the transducer back to the PIM and IVUS processing components, while the pulser delivers high voltage pulses directly to the transducer without the significant cable losses experienced in a conventional rotational IVUS system.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A rotational intravascular ultrasound (IVUS) device, comprising:
   a flexible elongate member;
   a piezoelectric micromachined ultrasound transducer (PMUT) coupled to a distal portion of the flexible elongate member;
   an application-specific integrated circuit (ASIC) coupled to the distal portion of the flexible elongate member, wherein the ASIC is electrically coupled to the PMUT and wherein the ASIC includes:
      a pulser for driving the PMUT,
      an amplifier for receiving and amplifying signals representative of ultrasound echoes received by the PMUT,
      a protection circuit configured to protect the amplifier from high voltage transmit pulses from the pulser and allow the amplifier to receive the low amplitude echo signals from the PMUT, and timing and control circuitry for coordinating operation of the pulser, amplifier, and protection circuit; and
   a four-lead electrical cable, wherein a distal portion of the four-lead electrical cable is electrically coupled to the ASIC;
   wherein the four-lead electrical cable is arranged to include two pairs of balanced signal leads.

2. The device of claim 1, wherein a proximal portion of the four-lead electrical cable is coupled to a connector configured to connect the four-lead electrical cable to a patient interface module (PIM).

3. The device of claim 1, wherein the four-lead electrical cable is shielded.

4. The device of claim 1, wherein each of the balanced signal lead pairs operates in a differential mode.

5. The device of claim 1, wherein each pair of balanced signal leads consists of a diagonally opposed pair of conductors such that the four-lead electrical cable is arranged in a star quad configuration.

6. A rotational intravascular ultrasound (IVUS) device, comprising:
   a flexible elongate member;
   a piezoelectric micromachined ultrasound transducer (PMUT) coupled to a distal portion of the flexible elongate member;
   an application-specific integrated circuit (ASIC) coupled to the distal portion of the flexible elongate member, wherein the ASIC is electrically coupled to the PMUT and wherein the ASIC includes:
      a pulser for driving the PMUT,
      an amplifier for receiving and amplifying signals representative of ultrasound echoes received by the PMUT,
      a protection circuit configured to protect the amplifier from high voltage transmit pulses from the pulser and allow the amplifier to receive the low amplitude echo signals from the PMUT, and
      timing and control circuitry for coordinating operation of the pulser, amplifier, and protection circuit; and
   a three-lead, shielded electrical cable, wherein a distal portion of the three-lead, shielded electrical cable is electrically coupled to the ASIC such that a pair of the three leads forms a balanced transmission line and the remaining lead and the shield form an unbalanced transmission line.

7. The device of claim 6, wherein the PMUT is formed on a microelectromechanical system (MEMS) component.

8. The device of claim 7, wherein the ASIC is flip-chip bonded to the MEMS component.

9. The device of claim 7, wherein the ASIC is wire bonded to the MEMS component.

10. The device of claim 7, wherein the ASIC is integrally formed with the MEMS component such that the ASIC and the MEMS component form a monolithic structure.

11. The device of claim 7, wherein the MEMS component and the ASIC are electrically coupled to a flex circuit substrate.

12. A rotational intravascular ultrasound (IVUS) system, comprising:
   an imaging device comprising:
      a flexible elongate member having a proximal portion and a distal portion;
      a proximal connector coupled to the proximal portion of the flexible elongate member;
      a piezoelectric micromachined ultrasound transducer (PMUT) coupled to the distal portion of the flexible elongate member;
      an application-specific integrated circuit (ASIC) coupled to the distal portion of the flexible elongate member, wherein the ASIC is electrically coupled to the PMUT and wherein the ASIC includes:
         a pulser for driving the PMUT,
         an amplifier for receiving and amplifying signals representative of ultrasound echoes received by the PMUT,
         a protection circuit configured to protect the amplifier from high voltage transmit pulses from the pulser and allow the amplifier to receive the low amplitude echo signals from the PMUT, and
         timing and control circuitry for coordinating operation of the pulser, amplifier, and protection circuit; and
      a four-lead electrical cable extending between the proximal connector and the distal portion of the elongate body, wherein a distal portion of the four-lead electrical cable is electrically coupled to the ASIC;
      wherein the four-lead electrical cable is arranged to include a pair of balanced signal leads;
   an interface module configured to connect with the proximal connector of the imaging device; and an intravascular ultrasound (IVUS) processing component in communication with the interface module.

13. The system of claim 12, wherein a proximal portion of the four-lead electrical cable is coupled to the proximal connector.

14. The system of claim 12, wherein the four-lead electrical cable is shielded.

15. The system of claim 12, wherein the PMUT is formed on a microelectromechanical system (MEMS) component.

16. The system of claim 15, wherein the ASIC is flip-chip bonded to the MEMS component.

17. The system of claim 15, wherein the ASIC is wire bonded to the MEMS component.

18. The system of claim 15, wherein the ASIC is integrally formed with the MEMS component such that the ASIC and the MEMS component form a monolithic structure.

19. The system of claim 15, wherein the MEMS component and the ASIC are electrically coupled to a flex circuit substrate.

20. The system of claim 12, wherein the balanced signal leads operate in a differential mode.

21. The system of claim 12, wherein the four-lead electrical cable is arranged to include two pairs of balanced signal leads.

22. A rotational intravascular ultrasound (IVUS) system, comprising:
an imaging device comprising:
a flexible elongate member having a proximal portion and a distal portion;
a proximal connector coupled to the proximal portion of the flexible elongate member;
a piezoelectric micromachined ultrasound transducer (PMUT) coupled to the distal portion of the flexible elongate member;
an application-specific integrated circuit (ASIC) coupled to the distal portion of the flexible elongate member, wherein the ASIC is electrically coupled to the PMUT and wherein the ASIC includes:
a pulser for driving the PMUT,
an amplifier for receiving and amplifying signals representative of ultrasound echoes received by the PMUT,
a protection circuit configured to protect the amplifier from high voltage transmit pulses from the pulser and allow the amplifier to receive the low amplitude echo signals from the PMUT, and
timing and control circuitry for coordinating operation of the pulser, amplifier, and protection circuit; and
a three-lead, shielded electrical cable, wherein a distal portion of the three-lead, shielded electrical cable is electrically coupled to the ASIC such that a pair of the three leads form a balanced transmission line and the remaining lead and the shield form an unbalanced transmission line;
an interface module configured to connect with the proximal connector of the imaging device; and
an intravascular ultrasound (IVUS) processing component in communication with the interface module.

23. A method of forming a rotational intravascular imaging device, comprising:
providing a piezoelectric micromachined ultrasound transducer (PMUT) coupled to the distal portion of the flexible elongate member;
providing an application-specific integrated circuit ASIC that includes:
a pulser for driving the PMUT,
an amplifier for receiving and amplifying signals representative of ultrasound echoes received by the PMUT,
a protection circuit configured to protect the amplifier from being damaged by high voltage transmit pulses from the pulser and allow the amplifier to receive the low amplitude echo signals from the PMUT, and
timing and control circuitry for coordinating operation of the pulser, amplifier, and protection circuit;
electrically coupling the PMUT and the ASIC; securing the PMUT and the ASIC to a distal portion of a flexible elongate member sized and shaped for insertion into human vasculature;
providing a four-lead electrical cable; and
electrically coupling a distal portion of the four-lead electrical cable to the ASIC; and
electrically coupling a proximal portion of the four-lead electrical cable to a proximal connector positioned at a proximal portion of a flexible elongate member, wherein the four-lead electrical cable is arranged to include two pairs of balanced signal leads.

24. A method of forming a rotational intravascular imaging device, comprising:
providing a piezoelectric micromachined ultrasound transducer (PMUT) coupled to the distal portion of the flexible elongate member;
providing an application-specific integrated circuit ASIC that includes:
a pulser for driving the PMUT,
an amplifier for receiving and amplifying signals representative of ultrasound echoes received by the PMUT,
a protection circuit configured to protect the amplifier from being damaged by high voltage transmit pulses from the pulser and allow the amplifier to receive the low amplitude echo signals from the PMUT, and
timing and control circuitry for coordinating operation of the pulser, amplifier, and protection circuit;
electrically coupling the PMUT and the ASIC;
securing the PMUT and the ASIC to a distal portion of a flexible elongate member sized and shaped for insertion into human vasculature;
providing a three-lead, shielded electrical cable;
electrically coupling a distal portion of the three-lead, shielded electrical cable to the ASIC such that a pair of the three leads forms a balanced transmission line and the remaining lead and the shield form an unbalanced transmission line; and
electrically coupling a proximal portion of the three-lead, shielded electrical cable to a proximal connector positioned at a proximal portion of a flexible elongate member.

25. The method of claim 24, further comprising positioning the flexible elongate member with the PMUT and the ASIC secured thereto within a lumen of a catheter such that the PMUT is positioned adjacent an ultrasound window of a distal portion of the catheter.

* * * * *